US009891153B2

(12) United States Patent
Abbad et al.

(10) Patent No.: US 9,891,153 B2
(45) Date of Patent: Feb. 13, 2018

(54) EVALUATION OF FLUID-PARTICLE MIXTURES BASED ON DIELECTRIC MEASUREMENTS

(71) Applicant: SCHLUMBERGER TECHNOLOGY CORPORATION, Sugar Land, TX (US)

(72) Inventors: Mustapha Abbad, Al-Khobar (SA); Khaled Hadj-Sassi, Al-Khobar (SA); Stephen Dyer, Al-Khobar (SA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 366 days.

(21) Appl. No.: 14/032,076

(22) Filed: Sep. 19, 2013

(65) Prior Publication Data
US 2015/0075272 A1 Mar. 19, 2015

(51) Int. Cl.
*E21B 47/005* (2012.01)
*E21B 49/08* (2006.01)
(Continued)

(52) U.S. Cl.
CPC ............. *G01N 15/00* (2013.01); *C09K 8/426* (2013.01); *E21B 47/102* (2013.01); *G01N 2015/0092* (2013.01)

(58) Field of Classification Search
CPC .................................................. E21B 47/0005
See application file for complete search history.

(56) References Cited

U.S. PATENT DOCUMENTS 2,211,688 A * 8/1940 Byck .................. C09K 8/22
166/294
3,115,197 A * 12/1963 Larsen .................. C09K 8/16
175/50
(Continued)

FOREIGN PATENT DOCUMENTS

WO WO 2011073790 A2 * 6/2011 ............. G01N 21/33

OTHER PUBLICATIONS

George, Matthew, Fred Growcock, and Ramadan Ahmed. Stability and Flow Behavior of Fiber-Containing Drilling Sweeps. INTECH Open Access Publisher, Mar. 2012.*
(Continued)

*Primary Examiner* — R. A. Smith
*Assistant Examiner* — Herbert K Roberts (57) ABSTRACT

A system is described for evaluating coagulation of particles in a downhole fluid-particle mixture based on dielectric measurements. An example downhole treatment is one in which flocs are used to plug a high-permeability subterranean formation zone as part of a stimulation procedure. An injection tube is positioned within the wellbore to the high-permeability zone. An instrumented section of tubing includes one or more dielectric probes that are positioned and configured to make dielectric measurements of the particle-fluid mixture flowing in the tubing or in the annulus. The downhole dielectric measurements are used to indicate whether or not the particle-fluid mixture has the desired structural properties. An operator on the surface can make adjustments in real-time according to the received dielectric measurements.

21 Claims, 4 Drawing Sheets

(51) Int. Cl.
*C09K 8/42* (2006.01)
*G01N 15/00* (2006.01)
*E21B 47/10* (2012.01)

(56) References Cited

U.S. PATENT DOCUMENTS

| | | | | | |
|---|---|---|---|---|---|
| 3,399,133 | A | * | 8/1968 | Gerdes | C02F 1/52 137/2 |
| 3,687,200 | A | * | 8/1972 | Routson | C09K 8/887 166/275 |
| 4,483,393 | A | * | 11/1984 | More | E21B 17/003 166/65.1 |
| 5,335,542 | A | * | 8/1994 | Ramakrishnan | E21B 33/1246 166/250.02 |
| 5,952,561 | A | * | 9/1999 | Jaselskis | E01C 19/288 73/78 |
| 6,330,916 | B1 | * | 12/2001 | Rickards | C09K 8/685 166/280.2 |
| 6,501,072 | B2 | * | 12/2002 | Mullins | E21B 47/102 250/255 |
| 8,016,038 | B2 | * | 9/2011 | Goodwin | E21B 47/10 166/264 |
| 2002/0056312 | A1 | * | 5/2002 | Tamura | B01J 8/1809 73/61.71 |
| 2003/0011386 | A1 | * | 1/2003 | Xie | G01N 22/00 324/694 |
| 2006/0226857 | A1 | * | 10/2006 | Troxler | G01N 27/223 324/663 |
| 2007/0051507 | A1 | * | 3/2007 | Ross | E21B 34/06 166/51 |
| 2007/0061082 | A1 | * | 3/2007 | Seleznev | G01V 3/26 702/11 |
| 2010/0073001 | A1 | * | 3/2010 | Benischek | E21B 43/16 324/334 |
| 2011/0000713 | A1 | * | 1/2011 | Meeten | E21B 47/102 175/40 |
| 2011/0088915 | A1 | * | 4/2011 | Stanojcic | E21B 43/267 166/386 |
| 2011/0260736 | A1 | * | 10/2011 | Troxler | G01R 35/007 324/601 |
| 2012/0232859 | A1 | * | 9/2012 | Pomerantz | G01V 99/005 703/2 |
| 2015/0136963 | A1 | * | 5/2015 | Xie | G01N 21/33 250/256 |
| 2016/0139103 | A1 | * | 5/2016 | Basu | G01N 33/28 324/698 |
| 2017/0061048 | A1 | * | 3/2017 | Grace | G06F 17/5009 |

OTHER PUBLICATIONS

Jakobsen, Thorvald, and Kjetil Folgerø. "Dielectric measurements of gas hydrate formation in water-in-oil emulsions using open-ended coaxial probes." Measurement Science and Technology 8.9 (1997): 1006.*

* cited by examiner

EVALUATION OF FLUID-PARTICLE MIXTURES BASED ON DIELECTRIC MEASUREMENTS

FIELD

The subject disclosure generally relates to evaluation of fluid-particle mixtures based on dielectric measurements. In particular, the subject disclosure relates to evaluation of coagulation of particles and/or flocculation of fibers in oilfield treatment fluids using dielectric measurements.

BACKGROUND

Upstream oil field exploration and production operations, including drilling, completion, stimulation, water injection, and other fluid and gas injection processes, often require using chemical and solid materials to temporarily seal off regions of very high permeability rocks—also known as a "thief zones." In drilling and completion, sealing off thief zones prevents lost circulation of drilling and completion fluids. In stimulation and other production and recovery enhancing processes, sealing off thief zones improves the uniformity of the injected stimulation fluid entering the formations along the trajectory of the wellbore, leading to improved hydrocarbon production and recovery. Efficient plugging of the thief zones can lead to more optimal short-term treatments as well as tending to increase the long-term profitability of the hydrocarbon extraction from subterranean formation. If not properly designed, the materials injected into the well could fail to seal the thief zones, or worse, they could damage the formation permeability such that the reservoir could become substantially less productive.

In order to create strong plugs, viscous fluids containing fibers and/or solid particles are often mixed by surface equipment prior to the injection. The fibers and/or particles are expected to interact together and form strong flocs and/or clusters. The flocculation and the coagulation are known to be highly sensitive to the viscosity of carrying fluid, the injection rate and the concentration of certain additives. The quality control of the resulting mixture is completed by visual inspection on the surface. However, when injected into the formation, the operator has no indication about interaction of the dispersed phase even though it is a very important condition for an efficient placement of the treatment fluid. Indeed, an early flocculation/coagulation will plug the downhole equipment and a late one will result in an unsuccessful fluid placement.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method for evaluating coagulation of particles in a downhole fluid-particle mixture is described. The method includes: making dielectric measurements in a downhole location of a fluid mixture containing fluid and particles using one or more downhole dielectric probes; receiving dielectric measurement data representing the dielectric measurements of the fluid mixture; and evaluating coagulation of the particles in the downhole fluid-particle mixture based on the dielectric measurement data. According to some embodiments, the fluid mixture is flowing through an injection tubing section within borehole, and the dielectric probes are mounted flush with an inner wall of the tubing section and configured to make the dielectric measurements on the fluid mixture flowing through the tubing section. According to some embodiments, the fluid mixture is flowing in the annulus and the dielectric probes are mounted flush with the outer surface of the tubing section and configured to make the dielectric measurements on the fluid mixture flowing through the annulus.

According to some embodiments, the dielectric probes are mounted on injection, treatment or production pipelines and configured to make dielectric measurements of the fluid mixture flowing through the surface pipes.

The fluid mixture is mixed using a surface facility prior to injection downhole, or a least a portion of the fluid mixture can be mixed downhole. The particles can be proppant particles, and the evaluating of coagulation can be an evaluation of clustering of the proppant particles. According to some embodiments, the particles are fibers, and the evaluating of coagulation can be an evaluation of a degree of flocculation of the fibers. In addition, the particles can be a defined mixture of fibers and proppant. According to some embodiments, adjustments in the fluid-particle mixture can be made in real-time in response to the evaluation of coagulation of the particles. According to some embodiments, a reference dielectric measurement value can be obtained based on dielectric measurements carried out on the surface during a calibration procedure for a fluid having suitable structural properties; and the received dielectric measurement data is compared with the obtained reference measurement.

According to some embodiments, a system is described for evaluating coagulation of particles in a downhole fluid-particle mixture. The system includes: an instrumented downhole tubing section including one or more dielectric probes mounted and configured to make dielectric measurements of a fluid mixture containing fluid and particles; an electrical cable configured to transmit signals from the one or more dielectric probes to a surface facility; and a processing system configured to facilitate an evaluation of coagulation of the particles in the downhole fluid-particle mixture based at least in part on signals received from the one or more dielectric probes. According to some embodiments, the processing system can be configured to display data representing the signals such that an operator can make the evaluation of coagulation. According to some embodiments, at least one pair of probes is mounted on opposite sides of the tubing section.

According to some embodiments, a method is described for evaluating coagulation of particles in a fluid-particle mixture. The method includes: making dielectric measurements in a fluid mixture containing fluid and particles using dielectric probes; receiving dielectric measurement data representing the dielectric measurements of the fluid mixture; and evaluating coagulation of the particles in the fluid-particle mixture based on the dielectric measurement data. According to some embodiments, the fluid mixture is mixed using a surface facility prior to injection into a borehole, and the dielectric probes are positioned at the surface facility to make the dielectric measurements of the fluid mixture prior to injection into the borehole. According to some embodiments, the dielectric probes are mounted so as to make dielectric measurements on the fluid-particle mixture prior to flowing through a disruption (such as an elbow, choke, pump, wellhead, or meter) in a surface flow line and the evaluation of coagulation is an evaluation of potential for clogging of the disruption from the particles.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein:

FIGS. 2-1 and 2-2 illustrate further details of a system for evaluating coagulation of particles in a downhole fluid-particle mixture based on dielectric measurements, according to some embodiments;

FIGS. 3-1 and 3-2 illustrate further details of a system for evaluating coagulation of particles in a downhole fluid-particle mixture based on dielectric measurements, according to some other embodiments.

DETAILED DESCRIPTION

The particulars shown herein are by way of example and for purposes of illustrative discussion of the embodiments of the subject disclosure only, and are presented in the cause of providing what is believed to be the most useful and readily understood description of the principles and conceptual aspects of the subject disclosure. In this regard, no attempt is made to show structural details in more detail than is necessary for the fundamental understanding of the subject disclosure, the description taken with the drawings making apparent to those skilled in the art how the several forms of the subject disclosure may be embodied in practice. Furthermore, like reference numbers and designations in the various drawings indicate like elements.

Figure 1:
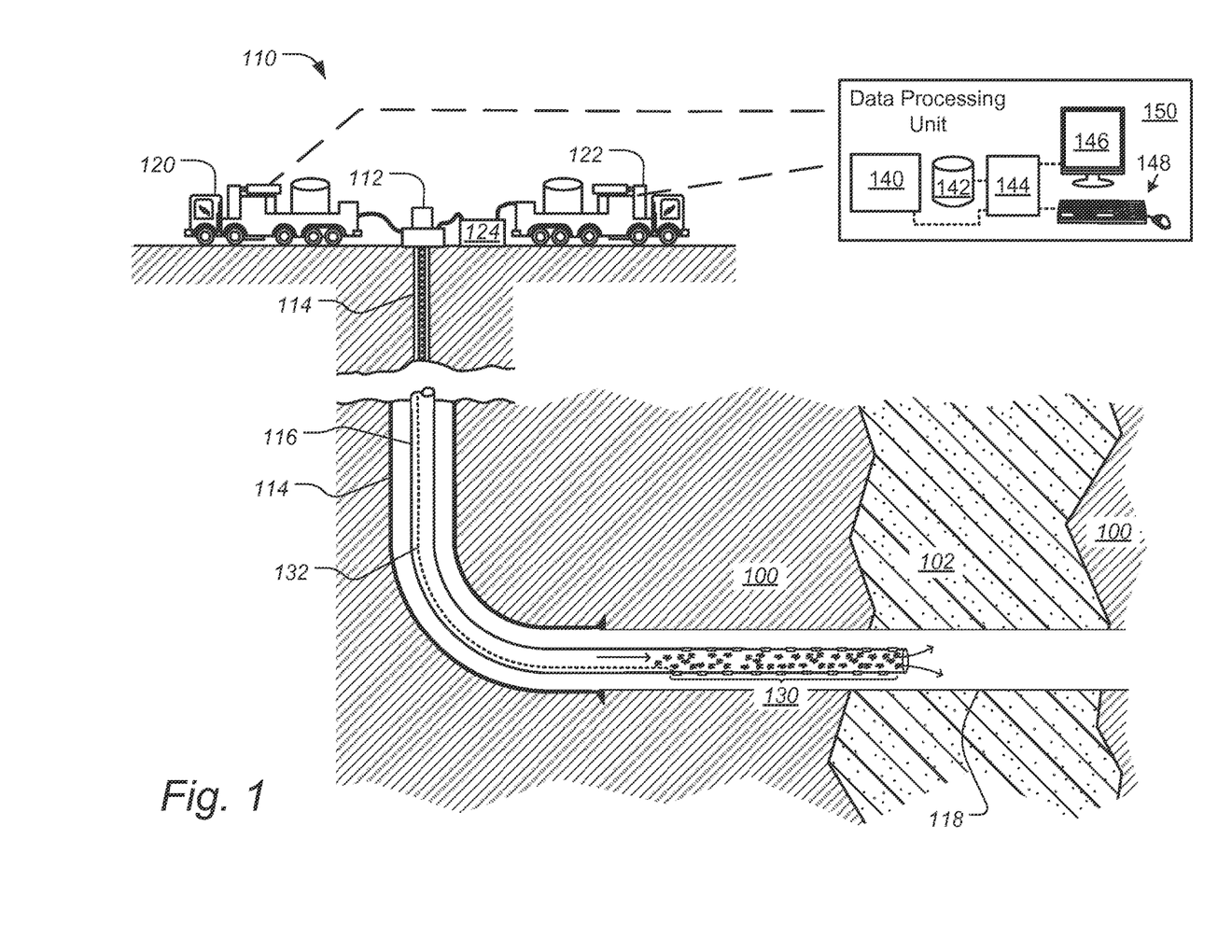
FIG. 1 illustrates a system for evaluating coagulation of particles in a downhole fluid-particle mixture based on dielectric measurements, according to some embodiments.

FIG. 1 illustrates a system for evaluating coagulation of particles in a downhole fluid-particle mixture based on dielectric measurements, according to some embodiments. FIG. 1 shows a downhole treatment in which flocs (coagulated masses of particles in a liquid) are being used to plug a subterranean formation zone 102. An injection tubing 116 is positioned within wellbore 114 that extends from the well head 112 on the surface to a subterranean rock formation 100 as well at to high-permeability zone 102. Equipment at the wellsite 110 include one or more service vehicles, such as trucks 120 and 122, as well as mixing and pumping equipment 124. In the example shown, the trucks 120 and 122 and equipment 124 are being used to deliver a particle-fluid mixture via injection tubing 116 to the target zone 102. Note that in the example shown wellbore 114 has an uncased section 118 in the vicinity of zone 102. According to some embodiments, the particles in the particle-fluid mixture are fibers which when coagulated, or flocculated, form flocs using to seal zone 102. An instrumented section 130 of tubing 116 includes one or more dielectric probes that are positioned and configured to make dielectric measurements of the particle-fluid mixture flowing in the section 130 of tubing 116. According to some embodiments, the instrumented tubing 116 is permanently or semi-permanently installed in wellbore 114 and according to other embodiments the tubing 116 installed in wellbore 114 for the stimulation treatment shown. According to some embodiments, downhole dielectric constant measurements from section 130 are used to indicate the dispersion state of fibers and solid particles in the injection tubing 116. The dielectric information is thus considered as a tool/technique to monitor the status of the injected fibers within the tubing 116 (or according to some other embodiments within the annulus space outside of tubing 116 within the wellbore). The signal acquired by the operators at the wellsite 110, via communication cable 132, is used to indicate whether the fibers and/or particles are individually dispersed in the fluid or they are flocculated and moving as clusters. Such an indication gives the operators more control than previously available in tailoring the treatment fluid on the fly, if desired.

According to some embodiments, the particle (e.g. fibers) and one or more fluid components are mixed on the surface at wellsite 110 before being pumped downhole through tubing 116. In such cases the mixture is often evaluated, such as by visual inspection, on the surface. However, when injected into the formation, the operator has no indication about interaction of the dispersed phase. For example, the viscosity of the particle-fluid mixture may be altered by temperature fluctuations downhole and this may in-turn have an impact on the state of coagulation/flocculation within the fluid. The downhole dielectric measurements are therefore very beneficial in monitoring and making real-time adjustments in the treatment being administered.

Figure 31:
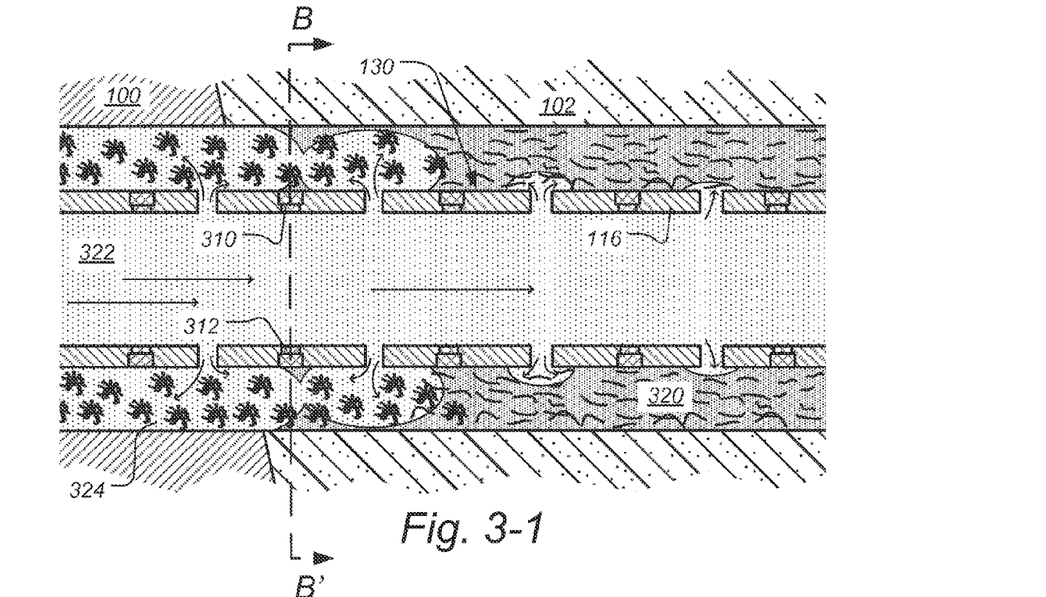
Figure 32:
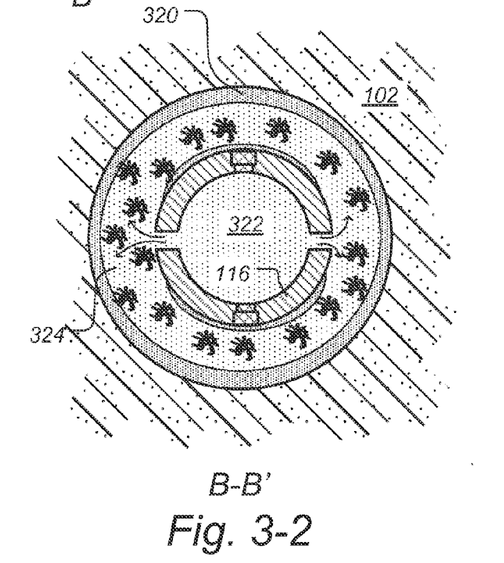

According to some embodiments, the particles (e.g. fibers) and one or more of the fluid components may be mixed downhole. For example, a carrier fluid can be mixed with the fibers on the surface and at a downhole location another fluid, such as water or other additive is introduced. In such cases downhole monitoring of the coagulation/flocculation within the fluid is highly desirable. In one such example, one of the wellsite trucks 120 or 122 is a coiled tubing truck that delivers tubing 116 into wellbore 114. The instrumented portion of the tubing 130, which can include multiple fluid delivery ports (not shown), is positioned at or near the target zone 102. In some examples, the tubing carries a first fluid, such as water, while a second fluid carrying the fibers is delivered through the annulus. In this example, the dielectric probes in section 130 are directed outwards since the coagulation is occurring in the annulus. Further details of such an example is shown in FIGS. 3-1 and 3-2, infra.

Although the example shown in FIG. 1 is been thus far described in the context of well stimulation, according to some embodiments the technique is also applied to other hydrocarbon exploration, production and recovery processes, such as drilling and well completions. For example, according to some embodiments the dielectric measurement data is used to evaluate the particle-fluid mixture of a fluid being used to seal a high permeability zone during a drilling operation so as to control circulation loss (loss of drilling fluid to a formation).

Also shown in FIG. 1 is data processing unit 150, which according to some embodiments includes a central processing system 144, a storage system 142, communications and input/output modules 140, a user display 146 and a user input system 148. The data processing unit 150 may be located in on or the other of trucks 120 and 122 and/or may be located in other facilities at wellsite 110 or in some remote location. The processing unit 150 is used to record and evaluate the data from the dielectric probes in the instrumented tubing section 130.

FIGS. 2-1 and 2-2 illustrate further details of a system for evaluating coagulation of particles in a downhole fluid-particle mixture based on dielectric measurements, according to some embodiments. Dielectric probes 210, 212, 214, 216 and 218 are shown flush-mounted in instrumented section 130 of the injection tubing 116. According to some embodiments, the probes are mounted on two sides of the tubing 116 and directed inwardly in order to obtain an accurate average of the dielectric constant (relative permittivity of the mixture) flowing through section 130 of tubing 116. According to some embodiments, the fiber mixture can also be injected through the annulus when the tubing is used to inject other treatment fluid (such as shown in FIGS. 3-1 and 3-2, infra). In that case, the measurement side of the probes are directed toward the annulus space between the tubing and the surface of the wellbore. The electrical circuit of the probes is powered from the surface 110 through a cabling 132 inserted in the wall of the injection tubing 116 such as shown in FIG. 1. According to some embodiments, the cable 132 is inserted into separate flexible pipe deployed downhole. According to some embodiments, the dielectric probes are calibrated prior to the job in order to obtain the signature of the desired structure of the fluid. When the mixture is injected downhole and the acquired dielectric signal is different from the calibrated signature, the operator can in real-time, iteratively correct the composition of the treatment until the target signature is acquired. In the example shown in FIG. 2-1, the downstream portion 230 of the fiber-fluid mixture in tubing 116 consists of un-coagulated dispersed fibers. The operators on the surface recognize this based on the dielectric measurements, and make a correction to the mixture. In response, the upstream portion 232 of the mixture contains flocs that can be confirmed via the dielectric measurements. FIG. 2-2 shows a cross section of tubing 116 along the line A-A'.

FIGS. 3-1 and 3-2 illustrate further details of a system for evaluating coagulation of particles in a downhole fluid-particle mixture based on dielectric measurements, according to some other embodiments. In this case, a fiber containing fluid 320 is pumped into the annulus of wellbore 114 outside of tubing 116. A second fluid 322, for example water, is pumped through the tubing 116. The instrumented section 130 of tubing 116 includes several fluid ports that allow fluid 322 to exit the tubing 116 and mix with the fiber-containing fluid 320. As a result of the addition of fluid 322, the fibers coagulate (flocculate) into flocs as shown in FIG. 3-1. The instrumented section 130 of tubing 116 includes multiple dielectric probes, such as probes 301 and 312, that are flush-mounted so as to be directed outward, towards the annulus. According to some embodiments, the tubing 116 can be delivered via coiled tubing. FIG. 3-2 shows a cross section of tubing 116 along the line B-B'.

Figure 4:
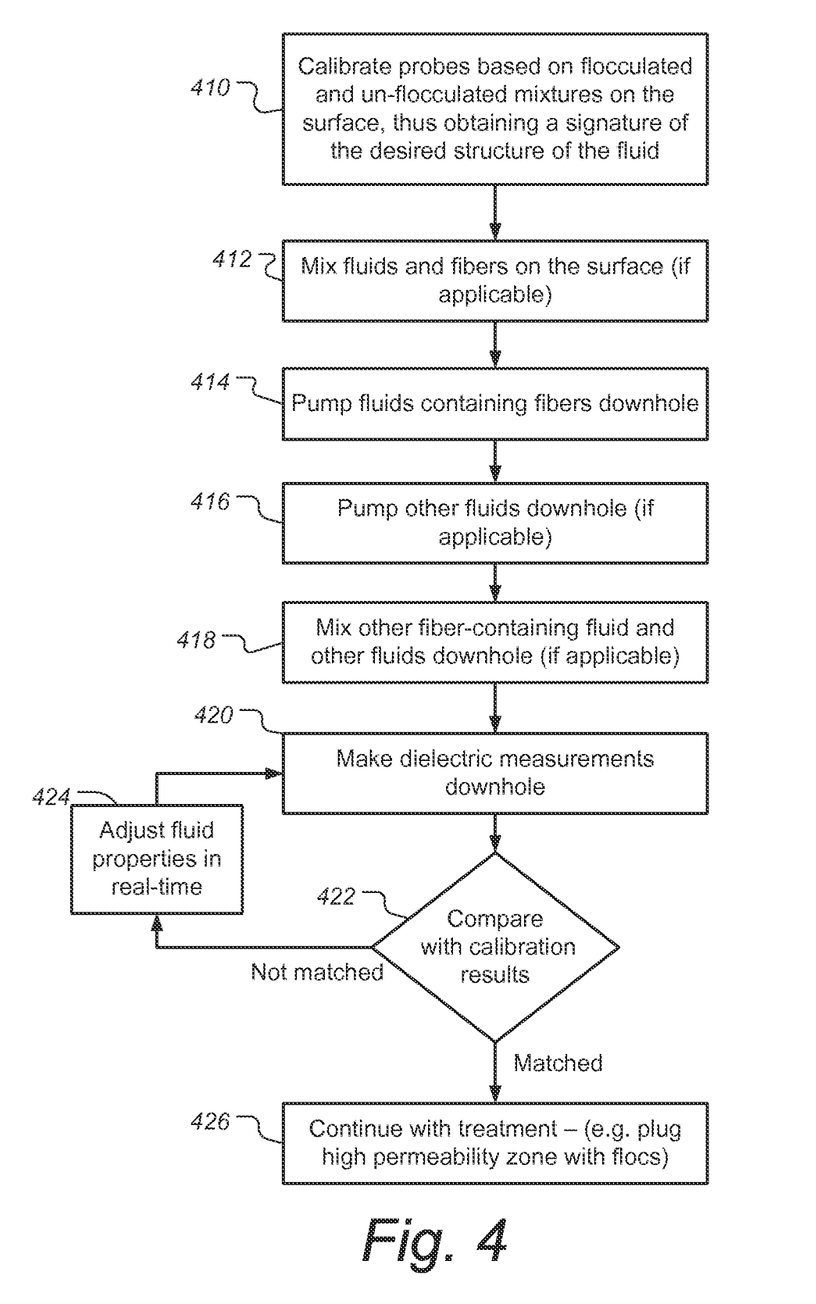
FIG. 4 is a flow chart illustrating aspects of evaluating the coagulation of particles in a downhole fluid-particle mixture based on dielectric measurements, according to some embodiments.
Figure 21:
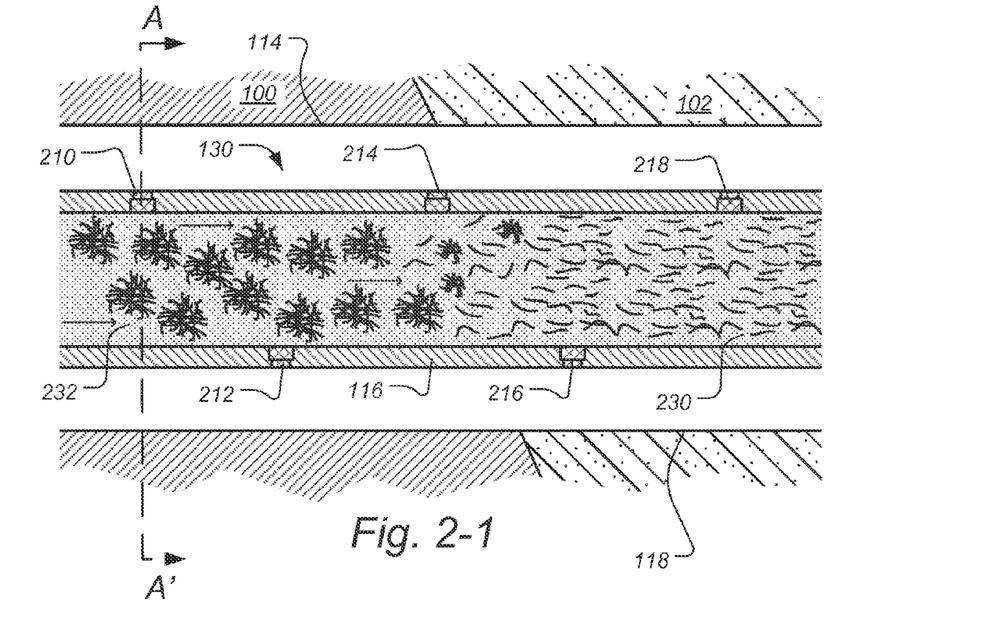
Figure 22:
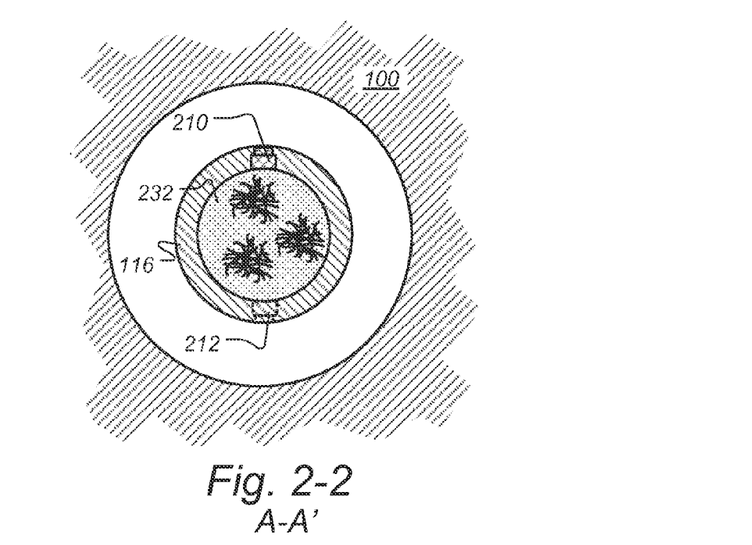

FIG. 4 is a flow chart illustrating aspects of evaluating the coagulation of particles in a downhole fluid-particle mixture based on dielectric measurements, according to some embodiments. In block 410, a calibration is carried out with the fibers (or other particles, such as proppants) in the fluids. A calibration signature is obtained using dielectric probes for the coagulated mixture having the desired structural properties. In block 412, fluids and particles (such as fibers) are mixed on the surface. According to some embodiments, some of the fluid ingredients are not mixed on the surface but rather are mixed downhole. In block 414, the fluids, including the fiber containing fluid, is pumped downhole. In block 416, other fluid(s) are pumped downhole, if further mixing is to be carried out downhole, which is undertaken in block 418 (if applicable). In block 420, the fiber containing fluid is measured using one or more downhole dielectric probes. Note the measurement can be taken within an injection tube (such as shown in FIGS. 2-1 and 2-2) or in the annulus (as shown in FIGS. 3-1 and 3-2). In decision block 422, the measurement results from block 420 are compared with the calibration results of block 410. If a sufficient match is present, the treatment is continued, for example temporary plugging of a high-permeability zone with the floc-containing fluid. If a sufficient match is not present, the operator on the surface makes adjustments in real time in block 424 and dielectric measurement continues in block 422.

Details of laboratory experiments will now be provided in order to more fully describe certain embodiments. In an experiment, 4 aqueous solutions were prepared as shown in Table 1. S1 contains distilled water and the three others (S2, S3 and S4) contain distilled water with different concentrations of guar gum (0.5, 1 and 1.5% per weight). The purpose of adding guar gum is to viscosify the base fluid and to obtain solutions with different fiber flocculation rate (flocculation tendency is inversely proportional to the viscosity). It was observed that in the solutions S1 and S2 the fibers are well flocculated and bulk fluid seems more homogeneous than the solutions S3 and S4 where the fibers were individually dispersed. Before adding a constant concentration of fibers of 12 g/L, the viscosities of the 3 solutions containing the guar gum were measured. A summary of their respective compositions is given in Table 1.

TABLE 1

| Composition of test sample solutions | | | | |
|---|---|---|---|---|
| Solution code | S1 | S2 | S3 | S4 |
| DI Water (% Wt) | 100 | 99.5 | 99 | 98.5 |
| Guar (% Wt) | 0 | 0.5 | 1.0 | 1.5 |
| Fibers (g/L) | 12 | 12 | 12 | 12 |
| Viscosity at 200 $s^{-1}$ (cP) | 1 | 43.6 | 133.1 | 362.8 |

The relative dielectric permittivity was acquired over the range of frequency 0.5-3 GHz, for each of the 4 solutions. Note that this is the relative permittivity as it is normalized relative to that of free space. The frequency dependence of permittivity (or dispersion) of the four prepared solutions was measured. It was found that the permittivity dispersions of the four solutions were relatively flat in the range of 75-80. Thus, one frequency can be selected to report the dielectric value for each solution. The Maxwell-Wagner effect was found to be almost negligible, as there was only a single phase inclusion related to the molecular polarization of the dielectric mechanisms. The permittivity dispersions of the flocculated solutions S1 of S2 were within the experimental uncertainties indicating minor variations. This small variation of the permittivity responses could be also seen on the un-flocculated/dispersed fibers of solutions S3 and S4. However, there was a measurable difference in the permittivity response of the two sets of solutions S1-S2 and S3-S4 (the respectively flocculated and un-flocculated solutions). The permittivity response was found to be lower for the flocculated solutions compared to these with individually dispersed fibers. This demonstrates the sensitivity of the dielectric responses to the state of dispersion of the fibers with a given mixture.

According to some embodiments, the techniques described herein can be applied on the surface in the oilfield industry. For example, referring to FIG. 1, within mixing and pumping equipment 124, dielectric probes are configured to monitor the dielectric properties immediately downstream of a particle—fluid mixing system, while the processing unit 150 is configured to evaluate the fluid mixtures and adjust the mixing system parameters via a feedback control loop. According to some embodiments the dielectric probes can be mounted in other surface locations, for example for monitoring fluids flowing through surface flow lines, such as stimulation treatment lines, injection pipes or production lines. Referring to FIG. 1, for example the dielectric probes can be mounted on the flow line between equipment 124 and wellhead 112, and/or from trucks 120 and 122 to equipment 124. According to some embodiments, the processing unit 150 can be configured to evaluate the coagulation of the particles upstream of flow disruptions such as elbows, chokes, pumps, wellheads, meters or other sensitive materials that require protection from plugging particles.

According to some embodiments, the techniques described herein are applicable beyond the oilfield industry. In general, the techniques described herein can be used in applications including but not limited to food processing, waste water processing, solid separation plants, and paper/pulp processing.

Although only some example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method for evaluating coagulation of particles in a downhole fluid-particle mixture introduced into a borehole, the method comprising:
   making dielectric constant measurements at a certain frequency in a frequency domain in a downhole location of an introduced fluid mixture containing fluid and particles using one or more downhole dielectric probes;
   receiving dielectric constant measurement data representing said dielectric constant measurements of the introduced fluid mixture;
   evaluating coagulation of the introduced particles in the downhole fluid-particle mixture based at least in part on the dielectric constant measurement data; and
   adjusting a dispersion state of the downhole fluid-particle mixture iteratively based on a reference dielectric constant measurement.

2. The method according to claim 1, wherein the introduced fluid mixture is flowing through an injection tubing section within a borehole, and said one or more dielectric probes are mounted flush with an inner wall of said tubing section and configured to make said dielectric constant measurements on the introduced fluid mixture flowing through said tubing section.

3. The method according to claim 2, wherein said introduced fluid mixture is mixed using a surface facility prior to injection downhole.

4. The method according to claim 1, wherein the introduced fluid mixture is flowing in an annulus at least partially defined by an outer surface of said tubing section and a borehole wall, and said one or more dielectric probes are mounted flush with said outer surface of the tubing section and configured to make said dielectric constant measurements on the introduced fluid mixture flowing through said annulus.

5. The method according to claim 4, wherein at least a portion of the introduced fluid mixture is mixed downhole.

6. The method according to claim 5, wherein said tubing section includes a plurality of ports configured to allow fluid within tubing to mix with fluid in the annulus.

7. The method according claim 1, wherein said introduced particles are proppant particles, and said evaluating coagulation is an evaluation of clustering of said proppant particles.

8. The method according to claim 1, wherein said introduced particles are fibers, and said evaluating coagulation is an evaluation of a degree of flocculation of said fibers.

9. The method according to claim 1, further comprising making one or more adjustments in said fluid-particle mixture in real-time in response to said evaluating coagulation of the introduced particles.

10. The method according to claim 1, wherein said dielectric constant measurement is a measurement of dielectric permittivity at a frequency within the range of 0.5-3 Ghz.

11. The method according to claim 1 further comprising:
   obtaining the reference dielectric measurement value based on dielectric measurements carried out on the surface during a calibration procedure for a fluid having suitable structural properties; and
   comparing the received dielectric measurement data with the obtained reference measurement, wherein said evaluation is based at least in part on said comparison.

12. The method according to claim 1, wherein said introduced fluid mixture is mixed using a surface facility prior to injection into a borehole, and said one or more dielectric probes are positioned at the surface facility to make said reference dielectric constant measurements of the fluid mixture prior to injection into the borehole.

13. A system for evaluating coagulation of particles in a downhole fluid-particle mixture introduced into a borehole, the system comprising:
   an instrumented downhole tubing section including one or more dielectric probes mounted and configured to make dielectric constant measurements at a certain frequency in a frequency domain of an introduced fluid mixture containing fluid and particles;
   an electrical cable configured to transmit signals from the one or more dielectric probes to a surface facility;
   a processing system configured to perform an evaluation of coagulation of the introduced particles in the downhole fluid-particle mixture based at least in part on signals received from the one or more dielectric probes; and
   adjusting a dispersion state of the downhole fluid-particle mixture iteratively based on a reference dielectric constant measurement.

14. The system according to claim 13, wherein said one or more dielectric probes are mounted flush with an inner wall of said tubing section and configured to make said dielectric constant measurements on the introduced fluid mixture flowing through said tubing section.

15. The system according to claim 13, wherein said one or more dielectric probes are mounted flush with an outer surface of the tubing section and configured to make said dielectric constant measurements on the introduced fluid mixture flowing through an annulus that is at least partially defined by said outer surface of said tubing section and a borehole wall.

16. The system according to claim 15 wherein said tubing section includes a plurality of ports configured to allow fluid within tubing to mix with fluid in the annulus.

17. The system according to claim 13, wherein said introduced particles are proppant particles, and said evaluation of coagulation is an evaluation of clustering of said proppant particles.

18. The system according to claim 13, wherein said introduced particles are fibers, and said evaluation of coagulation is an evaluation of a degree of flocculation of said fibers.

19. The system according to claim 13, wherein the processing system is configured to display data representing said signals such that an operator can make the evaluation of coagulation.

20. The system according to claim 13, wherein the one or more probes includes two probes.

21. The system according to claim 20, wherein the two probes are mounted on opposite sides of the tubing section.

* * * * *